United States Patent
Iversen (12) 
(10) Patent No.: US 6,365,577 B1
(45) Date of Patent: Apr. 2, 2002

(54) P53 ANTISENSE AGENT AND METHOD

(75) Inventor: Patrick L. Iversen, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

(21) Appl. No.: 09/426,804

(22) Filed: Oct. 22, 1999

Related U.S. Application Data (60) Provisional application No. 60/105,695, filed on Oct. 26, 1998.

(51) Int. Cl.[7] ............................ A01N 43/04; C12Q 1/68; C12N 15/63; C07H 21/00; C08B 3/00
(52) U.S. Cl. ............................ 514/44; 435/6; 435/91.1; 435/375; 435/455; 536/23.1; 536/24.5; 536/25.3; 536/31
(58) Field of Search ........................... 435/6, 91.1, 455, 435/366, 375; 536/23.1, 24.5, 31, 25.3; 514/44

(56) References Cited

U.S. PATENT DOCUMENTS 5,405,938 A * 4/1995 Summerton et al. ......... 528/406
5,968,909 A * 10/1999 Agrawal et al. ............... 514/44

FOREIGN PATENT DOCUMENTS

WO   WO 98/22142   5/1998

OTHER PUBLICATIONS

Karen Pihl–Carey, Isis To Restructure As Crohn's Disease Drug Fails In Phase III; Bioworld Today, The Daily Biotechnology Newspaper, vol. 10, No. 239 p. 1 of 5.*
Richard W. Wagner et al., Antisense Gene Inhibition by Oligonucleotides Containing C–5 Propyne Pyrimidines; Science, vol. 260, Jun. 4, 1993 pp. 1510–1513.*
Natalie Milner et al., Selecting effective antisense reagents on combinatorial oligonucleotide arrays; Nature Biotechnology, vol. 15, Jun. 1997 pp. 537–541.*
Stanley T. Crooke, Basic Principles of Antisense Therapeutics; pp. 1–50.*
Andrea D. Branch, A good antisense molecule is hard to find; TIBS 23, Feb. 1998, pp. 45–50.*
W. James, Towards gene–inhibition therapy: a review of progress and prospects in the field of antiviral antisense nucleic acids and ribozymes; Antiviral Chemistry & Chemotherapy, (1991) 2(4), pp. 191–214.*

Arora, V., "In vivo use of antisense phosphorothioate oligonucleotides to modulate P53 expression (oxidative damage, metallothionein)" University of Nebraska Medical Center Ph.D. Dissertation Abstract (1998).
Benner, E., et al., "Combination of Antisense Oligonucleotide and Low–Dose Chemotherapy in Hematological Malignancies" *Journal of Pharmacological and Toxicological Methods* 37:229–235 (1997).
Bonham, M.A., et al., "An assessment of the antisense properties of RNase H–competent and steric–blocking oligomers" *Nucleic Acids Research* 23(7):1197–1203 (1995).
Chen, J–K., et al., "Synthesis of oligodeoxyribonucleotide N3'→P5' phosphoramidates" *Nucleic Acids Research* 23(14):2661–2668 (1995).
Gee, J.E., et al., "Assessment of High–Affinity Hybridization, RNase H Cleavage, and Covalent Linkage in Translation Arrest by Antisense Oligonucleotides" *Antisense & Nucleic Acid Drug Development* 8:103–111 (1998).
Hudziak, R.M., et al., "Resistance of Morpholino Phosphorodiamidate Oligomers to Enzymatic Degradation" *Antisense & Nucleic Acid Drug Development* 6:267–272 (1996).
Mebmer, U.K., "Nitric Oxide–Induced Apoptosis in RAW 264.7 Macrophages is Antagonized by Protein Kinase C– and Protein Kinase A– Activating Compounds" *Molecular Pharmacology* 47:757–765 (1996).
Summerton J. and Weller, D., "Morpholino Antisense Oligomers: Design, Preparation, and Properties" *Antisense & Nucleic Acid Drug Development* 7:189–195 (1997).
Uhlmann, E. and Peyman, A., "Antisense Oligonucleotides: A New Therapeutic Principle" *Chemical Reviews* 90(4):543–584 (1990).
Wagner, R., et al., "Antisense Gene Inhibition by Oligonucleotides Containing C–5 Propyne Pyrimidines" *Science* 260:1510–1513 (1993).

* cited by examiner

Primary Examiner—Andrew Wang
Assistant Examiner—Jane Zara
(74) Attorney, Agent, or Firm—LeeAnn Gorthey

(57) ABSTRACT

Antisense oligonucleotides useful for treating a disease state characterized by p53 induction, such as proliferative cell disorders, e.g. cancer, or a hypoxic state induced by an ischemic attack, such as stroke, are described. The antisense agents are preferably of the class known as "steric blocker" type oligonucleotides, including morpholino oligonucleotides, peptide nucleic acids, 2'-O-allyl or 2'-O-alkyl modified oligonucleotides, or N3'→P5' phosphoramidate oligonucleotides.

18 Claims, 2 Drawing Sheets

P53 ANTISENSE AGENT AND METHOD

This application claims priority to Provisional Application No. 60/105,695 filed Oct. 26, 1998, now pending, which is incorporated herein by reference.

FIELD OF THE INVENTION

The present invention relates to antisense agents and methods for the treatment of disease states which are characterized by induction of p53. Such conditions include proliferative cell disorders, such as cancer, restenosis, and psoriasis, and hypoxic states induced by ischemic attacks such as stroke.

REFERENCES

Adhad, N. et al., *Biochem. Biophys. Res. Commun.* 247:294–301 (1998).
Agrawal, S. et al., *Proc. Natl. Acad. Sci. USA* 87(4):1401–5 (1990).
Arora, V., Ph.D. Dissertation, Dep. Pharmacol., Univ. Nebraska Coll. Med. (1998).
Assy, N. et al., "Use of proliferating cell nuclear antigen as a marker of liver regeneration after partial hepatectomy in rats," *J Lab Clin Med* 131(3):251–256 (1998).
Bonham, M. A. et al., *Nucleic Acids Res.* 23(7):1197–1203 (1995).
Boudvillain, M. et al., *Biochemistry* 36(10):2925–31 (1997).
Chen, J.-K. et al., *Nucleic Acids Res.* 23:2661–8 (1994).
Cross, S. M. et al., *Science* 267 (5202) p1353–6 (1995).I
Edelman, E. R. et al., *Circ. Res.* 76(2):176–182 (1995).
Farrell, C. L. et al., *Antisense Res. and Dev.* 5:175–183 (1995).
Gambacorti-Passerini, C. et al., *Blood* 88(4):1411–7 (1996).
Gee, J. E. et al., *Antisense & Nucleic Acid Drug Dev.* 8:103–111 (1998).
Giles, R. V. et al., *Anticancer Drug Des.* 8(1):33–51 (1993).
Graeber, T. G. et al., *Mol. Cell Biol.* 14(9):6264–77 (1994).
Grisham, J. W. et al., "Cell cycle and chemical carcinogenesis," *Surv. Synth. Pathol. Res.* 9–66 (1983).
Gryaznov, S. M. et al., *Proc. Natl. Acad. Sci. USA* 92:5798–5802 (1995).
Hanvey, J. C. et al., *Science* 258:1481–85 (1992).
Hartwell, L. H. and Kastan, M. B. "Cell cycle control and cancer," *Science* 266:1821–28 (1994).
Higgins, G. M. and Anderson, R. M. *Arch. Pathol.* 12:186. (1931).
Horiguchi et al., *Takeda Kenyushoho* 55:149–159 (1996).
Johansson, H. E. et al., *Nucleic Acids Res.* 22:4591–8 (1994).
Kanoh et al., *Bioorg. Chem. Lett.* 7:2847 (1997).
Kastan, M. B. et al., *Cell* 71: 587–97. (1992).
Khooustov, V. I., et al., *Lab. Invest.* 73:118–127 (1995).
Knudsen, H. and Nielsen, P. E., *Nucleic Acids Res.* 24(3):494–500 (1996).
Koch et al., *Biochem. Biophys. Res. Commun.* 225:531–536 (1996).
Levine, A. J. "p53, The cellular gatekeeper for growth and division," *Cell* 88:323–331 (1997).
Li, Y. et al., *Brain Res* 765 (2) p301–12 (1997).
Lu, X. and Lane, D. P., *Cell* 75(4):765–78 (1993).
Magnelli, L. et al., *Biochem Mol Med* 62(1):3–10 (1997).
Messmer, U. K. et al., "p53 Expression in nitric oxide-induced apoptosis", *FEBS Lett* 535(l):23–6 (1994).
Nelson, W. G. and Kastan, M. B., *Mol. Cell Biol.* 14: 1815–1823 (1994).
Nielsen, P. E. et al., *Science* 254:1497–1503 (1991).
Raafat, A. M. et al., *Shock Sep* 8 (3) p186–92 (1997).
Rininger, J. A. et al. "Time course comparison of cell-cycle protein expression following partial hepatectomy and WY 14,643-induced hepatic cell proliferation in F344 rats." *Carcinogenesis* 18(5):935–41 (1997).
Rosenberg, R. D. et al., U.S. Pat. No. 5,593,974 (1997).
Russell, K. J. et al., *Int. J. Radiat. Oncol. Biol. Phys.* 36(1099–1106 (1996).
Russo, A. et al., *Cancer Treatment Reports*, 69(11):1293–96 (1985).
Sato, F. et al., *Biochem. Biophys. Res. Commun.* 204:578–584 (1994).
Sedlacek et al., *Int. J. Oncol.* 9:1143–1168 (1996).
Shu, M. et al., *Apoptosis* 2:263–470 (1997).
Soini, T. et al., *Br. J. Dermatol.* 131(4):514–20 (1994).
Speir, E. et al., *Scand. J. Infect. Dis. Suppl.* 99:78–81 (1995).
Swe, M. et al., *Biochem. Biophys. Res. Commun.* 236:594–598 (1997).
Tadini, G. et al., *Acta Derm. Venereol Suppl.* 146:33–35 (1989).
Van Dolah, F. M. et al., *J. Cell Physiol.* 166:49–56 (1996).
Wagner, R. W. et al., *Science* 260:1510–13 (1993).
Waldman, T. et al., "Uncoupling of S phase and mitosis induced by anticancer agents in cells lacking p21," *Nature* 381:713–716 (1996).
Xiang, H. et al., *J Neurosci* 16 (21) p6753–65 (1996).
Zhang, M. and Raveche, E. S., *Oncol Rep* 5 (1) p23–30 (1998).
Zhu, W. Y. et al., *Exp. Cell Res.* 2:463–470 (1997).

BACKGROUND OF THE INVENTION

The importance of p53 in cell proliferation is apparent from the observation that more than half of all human cancers display p53 mutations (Levine, 1997). An induction in p53 expression is observed in cells exposed to DNA alkylating agents, nitric oxide (Messmer, 1994), ionizing and ultraviolet irradiation (Lu and Lane, 1993), the restriction enzyme PvuII, which induces chromosome damage (Lu and Lane, 1993), and other agents capable of inducing DNA strand breaks (Nelson and Kastan, 1994). Ischemia/reperfusion (Raafat, 1997), models of epilepsy (Xiang, 1996), and hypoxia (Graeber, 1994) have also been demonstrated to induce p53. As shown herein and in previous studies (Rininger, 1997), p53 protein levels are also highly upregulated during the course of liver regeneration following partial hepatectomy, showing that damage of endogenous origin can also cause induction of p53 in vivo.

Roles for p53 have been postulated in cell cycle checkpoint activity, apoptosis, differentiation and DNA repair (Magnelli, 1997). Cell cycle checkpoints serve two important functions. One is to ensure that essential events in the cell cycle are completed before a subsequent event; the other is to provide more time for repair of damaged DNA before DNA replication and mitosis occur (Hartwell, 1994). The checkpoint activity of p53 occurs predominantly at the level of cells entering the S-phase (DNA synthesis) of the cell cycle (Kastan, 1992). $G_2$-M checkpoint activity has also been reported for p53, due to its role as an upstream regulator of $p21^{waf-1}$. In the absence of either protein, DNA-damaged cells arrest in a $G_2$-like state, but then undergo additional S phases without intervening normal mitoses (M phase), leading to nuclear abnormalities, e.g. polyploidy, and culminating in apoptosis (Waldman,

SUMMARY OF THE INVENTION

The invention provides, in one aspect, methods and compositions for treating a disease state characterized by p53 induction in a mammalian subject. The method comprises administering to the subject, in a suitable pharmaceutical carrier, a pharmaceutically effective amount of an antisense agent having the base sequence SEQ ID NO: 1, identified as 5'-TCA GTC TGA GTC AGG CCC-3, or the base sequence SEQ ID NO:2, identified as 5'-CCC TGC TCC CCC CTG GCT CC-3', where the antisense agent is a morpholino oligonucleotide, a peptide nucleic acid, a 2'-O-allyl or 2'-O-alkyl modified oligonucleotide, a N3'→P5' phosphoramidate oligonucleotide, or a C-5-propyne pyrimidine-modified oligonucleotide. In a preferred embodiment, the antisense agent is a morpholino oligonucleotide, preferably having morpholino subunits joined by phosphorodiamidate backbone linkages. In another preferred embodiment, the antisense agent is a C-5-propyne pyrimidine-modified oligonucleotide.

The invention also includes compositions for use in treating such disease states. These compositions include antisense agents as described above, in a suitable pharmaceutical carrier.

In preferred applications of the method, the subject is a human subject. The disease state may be one which results from an ischemic or ischemic/reperfusive injury, such as stroke or the aftermath of organ transplant. Alternatively, the disease state may be cancer, in which case a preferred embodiment further comprises administering an agent effective to increase radical oxygen species at the cellular level. Such agents include radiosensitizing agents, ionizing radiation, a hyperbaric oxygen environment, and chemotherapeutic agents, such as certain anthracyclines or anthraquinones, which increase radical oxygen species at the cellular level.

For cancer treatment, the method may also include administering an agent effective to interfere with progression from the $G_2$ phase to the M phase of the cell cycle. Such agents include phosphokinase C (PKC) inhibitors, bis(chloroethyl) nitrosourea (BCNU), pentoxifylline, silymarin, staurosporine, phenylahistin, paclitaxel, retinoic acid, flavopiridol, methyl-2,5-dihydrocinnamate, herboxidiene, 9-nitrocamptothecin, maitotoxin, apigenin, nocodazole, and colcemid.

In another aspect, the invention provides an oligonucleotide having a base sequence selected from the group consisting of SEQ ID NO:1, identified as 5'-TCA GTC TGA GTC AGG CCC-3', and SEQ ID NO:2, identified as 5'-CCC TGC TCC CCC CTG GCT CC-3', where the oligonucleotide is selected from the group consisting of a morpholino oligonucleotide, a peptide nucleic acid, a 2'-O-allyl or 2'-O-alkyl modified oligonucleotide, and a N3'→P5' phosphoramidate oligonucleotide. In one embodiment, the oligonucleotide is a morpholino oligonucleotide, preferably comprising morpholino subunits joined by phosphorodiamidate backbone linkages. The invention also provides an oligonucleotide having a base sequence selected from the group consisting of SEQ ID NO: 1, identified as 5'-TCA GTC TGA GTC AGG CCC-3', and SEQ ID NO:2, identified as 5'-CCC TGC TCC CCC CTG GCT CC-3', where the oligonucleotide is a C-5-propyne pyrimidine-modified oligonucleotide.

These and other objects and features of the invention will become more fully apparent when the following detailed description of the invention is read in conjunction with the accompanying drawings.

DETAILED DESCRIPTION OF THE INVENTION

I. Definitions

An "antisense oligonucleotide" or "antisense agent" refers to a molecule which includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions which allow such hydrogen bonding. These backbone moieties are cyclic moieties of 5 to 7 atoms in length, linked together by phosphorous-containing linkages one to three atoms long.

Figure 1:
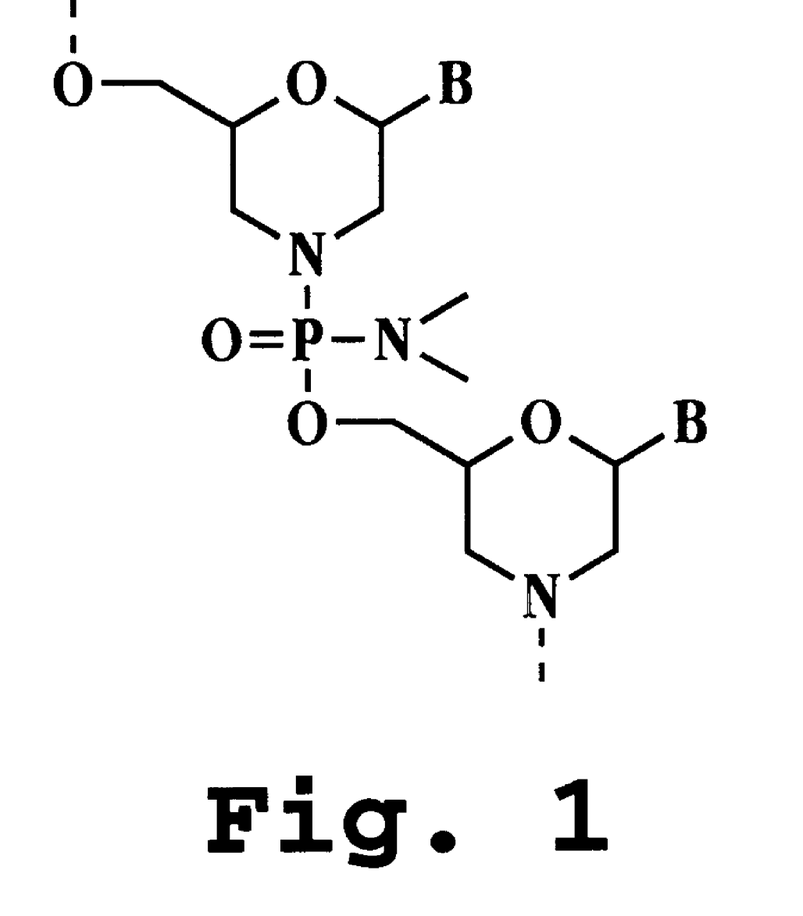
FIG. 1 shows the structure of a phosphorodiamidate-linked morpholino oligonucleotide analog.

A "morpholino" oligonucleotide is composed of morpholino subunit structures of the form shown in FIG. 1, where (i) the structures are linked together by phosphorous-containing linkages, one to three atoms long, joining the morpholino nitrogen of one subunit to the 5' exocyclic carbon of an adjacent subunit, and (ii) B is a purine or pyrimidine base-pairing moiety effective to bind, by base-specific hydrogen bonding, to a base in a polynucleotide. FIG. 1 illustrates two such subunits joined by a phosphorodiamidate linkage.

A "N3'→P5' phosphoramidate" oligonucleotide is one in which the 3'-oxygen of the 2'-deoxyribose is replaced by a 3'-amine, as described, for example, by Gryaznov et al. and Chen et al.

A "2'-O-allyl (or alkyl) modified oligonucleotide" is an oligoribonucleotide in which the 2' hydroxyl is converted to an allyl or alkyl ether. The alkyl ether is typically a methyl ether.

A "C-5-propyne pyrimidine-modified oligonucleotide" is an oligonucleotide in which the C-5 methyl group of thymidine bases and/or the C-5 hydrogen of cytidine bases has been replaced with a propyne group.

In a "peptide nucleic acid", the deoxyribose phosphate units of an oligonucleotide backbone are replaced with polyamide linkages. As described, for example, in Nielsen et al. and Hanvey et al., proper backbone spacing is attained by the use of 2-aminoethyl glycine units, with a nucleotide base attached to each 2-amino group via a methylenecarbonyl group.

A "RNAse-inactive" oligonucleotide or oligonucleotide analog is one which acts via an RNase-independent mechanism, unlike RNAse-active oligonucleotides, such as phosphorothioates. They are believed to function by sterically blocking target RNA formation, nucleocytoplasmic transport or translation, and are thus also referred to as "steric blockers". This class includes, for example, methylphosphonates, morpholino oligonucleotides, as described herein, peptide nucleic acids (PNA's), 2'-O-allyl or 2'-O-alkyl modified oligonucleotides, and N3'→P5' phosphoramidates.

A condition "characterized by induction of p53" is a disease state in which levels or expression of p53 protein in affected cells are increased relative to the non-disease state, and/or a condition in which suppression of p53 expression, sometimes in combination with other treatment, has a beneficial therapeutic effect. Examples are cancer, ischemia, such as results from stroke, myocardial infarction, or epileptic seizure, and the resulting hypoxic state, and ischemic/reperfusive injury, such as may occur in organ transplants. Abbreviations:

ON=oligonucleotide
ODN=oligodeoxyribonucleotide
S-ODN=phosphorothioate oligonucleotide
C-5-P=C-5-propyne pyrimidine-modified oligonucleotide

II. Antisense Oligonucleotides

A. Sequences

The antisense agents of the present invention comprise nucleotide subunits joined by internucleotide backbone linkages which present the nucleotide bases for hybridization with target RNA sequences. The base sequences of these agents are complementary (antisense) to portions of p53 mRNA. The first sequence, corresponding to SEQ ID NO: 1, is complementary to a unique portion of rat p53 mRNA (residues 1182 to 1199; Genbank accession # X13058) and is referred to herein as "p53T". This sequence is the same in rat, mouse, monkey, and human mRNA, and thus ideally suited for in vivo testing in animal models.

The second sequence, named "OL(1)p53" and corresponding to SEQ ID NO: 2, is antisense to human p53, and is therefore effective at inhibiting p53 expression in humans (Iverson, U.S. Pat. No. 5,641,754). Because it has four mismatches with the rat sequence, it does not alter such expression in rats, and therefore provides a useful control in rat model studies.

B. Oligonucleotide Structure

Various oligonucleotide analogs known in the art present advantages over "natural" polynucleotides in areas such as stability, particularly nuclease resistance, reduction of non-specific binding, and bioavailability (i.e. access to cells). The structures may be modified at the backbone, the sugar moiety, or the bases themselves. Such analogs include, for example, phosphorothioates (designated herein as S-ODN), methylphosphonates, phosphotriesters, C-5-propyne pyrimidine-modified oligonucleotides (C-5-P), morpholino oligonucleotides, peptide nucleic acids (PNA's), 2'-O-allyl or 2'-O-alkyl modified oligonucleotides, and N3'→P5' phosphoramidates.

Preparation of such antisense agents is well known in the art, and may often be conveniently carried out on automated synthesizers. A general procedure for synthesis of S-ODN, C-5-P, and uncharged morpholino antisense oligonucleotides is given in Example 1.

Two general mechanisms have been proposed to account for inhibition of expression by antisense oligonucleotides (see e.g. Agrawal; Bonham; Boudvillain; and references cited therein). In the first, a heteroduplex formed between the oligonucleotide and mRNA serves as a substrate for RNase H, leading to cleavage of the mRNA. Oligonucleotides belonging, or proposed to belong, to this class include phosphorothioates, phosphotriesters, and phosphodiesters (i.e., unmodified "natural" oligonucleotides). Such compounds generally show high activity, and phosphorothioates are currently the most widely employed oligonucleotides in antisense applications. However, these compounds tend to produce unwanted side effects due to non-specific binding to cellular proteins (Gee), as well as inappropriate RNase cleavage of non-target RNA heteroduplexes (Giles).

A second class of oligonucleotide analogs, termed "steric blockers" or, alternatively, "RNase inactive" or "RNase resistant", are not observed to activate RNase H, and are believed to act by sterically blocking target RNA formation, nucleocytoplasmic transport or translation. This class includes methylphosphonates (Toulme) as well as morpholino oligonucleotides, peptide nucleic acids (PNA's), 2'-O-allyl or 2'-O-alkyl modified oligonucleotides (Bonham), and N3'→P5' phosphoramidates (Gee). They are reported to be most effective when targeted at the AUG start codon, the 5'-splice site, or the 5'-untranslated region of mRNA's. To date, they have shown relatively weak (Bonham) or, more often, no activity when targeted downstream, at coding regions (see, for example, Toulme, for methylphosphonates; Gambacorti, for PNA's; Knudsen, for duplex-forming PNA's; and Gee, for PNA's and N3'→P5' phosphoramidates). It has been proposed that the hybrids formed by these ON's, when directed to the coding region, are not sufficiently stable to avoid being displaced by the unwinding action of the ribosomal complex during translation (Boudvillain, Gee). One approach to addressing this problem has been to covalently link or intercalate the ON to its target sequence (Gee, Johansson). However, without such modifications, the activity of steric blocking ON's has generally been limited to the initiation regions noted above.

III. Induction of p53 in Proliferating Cells and Suppression by Antisense p53

In previously reported studies (Arora, 1998), antisense agents p53T and ON(1)p53, described above, were administered to rats immediately after partial hepatectomy surgery, as described in Example 2. The regenerating rat liver is an excellent in vivo model system to study the mechanisms of growth control and cellular proliferation in a natural tissue environment. The rapidly proliferating cells in the regenerating liver are extremely susceptible to carcinogenesis, as there is minimal time available between cell cycles for DNA repair (Grisham, 1983). As noted above, ON(1)p53 does not alter p53 expression in rats, and was used as a control.

A massive induction of p53 was observed during the process of regeneration in the PH (post-hepatectomy) rats. The following effects of antisense ON administration were measured: weight gain of regenerating liver; level of p53, PCNA, p21 and NADPH; DNA content of isolated cells; microsomal protein content; various microsomal enzyme assays; oxidative stress, as evidenced by lipid peroxidation; and mitotic index.

When treated with antisense p53T (SEQ ID NO:1), the livers lost their $G_1$-S cell cycle checkpoint activity, as evidenced by increases (relative to controls) in weight gain, mitotic index, and PCNA expression, which is an accurate marker of cell proliferation (Assy, 1998), and a 5-fold reduction in $G_1$ cell population. The p53T-treated PH rat livers also displayed a greater number of multi-nucleate cells. Functional recovery of the regenerating liver, as determined by enzyme assays, was also increased by p53 inhibition.

In summary, the data showed that p53 expression is inhibited in regenerating livers of post-hepatectomy rats treated with antisense p53T (SEQ ID NO: 1), and that this inhibition results in enhanced mitosis, elevated PCNA expression, and diminished number of cells in the $G_1$ phase of the cell cycle. The results are consistent with $G_1$-S cell cycle checkpoint activity of p53.

IV. Comparative Effect of S-ODN, C-5-P, and Morpholino Antisense Agents

Neutral-backbone morpholino antisense agents having the base sequences given as SEQ ID NO: 1 and SEQ ID NO: 2 were prepared as described in Example 1. Such morpholino oligomers have shown high binding affinity for RNA targets, and the uncharged backbone favors uptake into cells and reduces non-specific binding interactions, relative to charged analogs such as phosphorothioates. Also prepared were the corresponding C-5-propyne cytosine modified (C-5-P) phosphorothioates. As discussed above, the morpholino analog is believed to act as a "steric blocker". C-5-P phosphorothioates are reported to act by an RNase-H dependent mechanism (Wagner), attributed to phosphorothioates in general.

Figure 2:
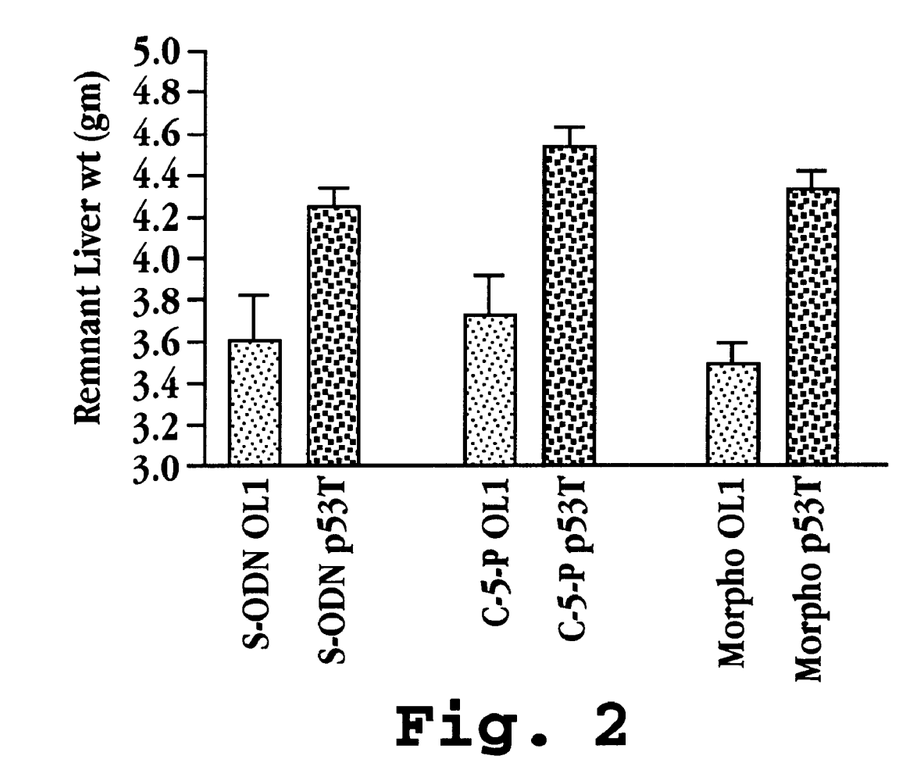
FIG. 2 shows the wet weights (in gm) of remnant regenerating livers in rats, 24 hr after partial hepatectomy and administration of the following antisense oligonucleotides, having SEQ ID NOs 1 and 2, respectively: a phosphorothioate (S-ODN, 1 mg/200 g); a C-5-P modified phosphorothioate (C-5-P, 0.1 mg/200 g); and a neutral backbone (phosphorodiamidate) morpholino oligonucleotide (3.4 mg/200 g). Error bars represent statistical difference of $p<0.05$ with respect to the saline-treated control of each respective group. In the Figure, the designation "p53T" corresponds to SEQ ID NO: 1, and the designation "OL1" corresponds to SEQ ID NO: 2.

The effect of intraperitoneal administration of these antisense agents was compared to that of the unmodified phosphorothioates (S-ODNs) with respect to wet weight gain of remnant regenerating livers 24 hr post PH, as described in Section III and Example 2. The data, shown in FIG. 2, indicate that the p53T sequence is active in the liver regeneration model for both of the alternate analogs tested, and the OL(1)p53 sequence remained inactive (as expected) with the alternate analogs at the doses tested.

Efficacy similar to a 1 mg/200 gm dose of S-ODN p53T was observed with 100 μg/200 gm of the C-5-P modified S-ODN and 50 nM/200 gm (approximately 3.7 mg/200 g) of the morpholino anti-p53T oligonucleotide (having SEQ ID NO: 1). It is especially noteworthy that the morpholino antisense oligomer is active when targeted to exon 10 of the coding region of the gene, rather than to the 5'-untranslated region or the AUG start codon. As noted above, "steric blocker" antisense agents generally have not shown significant activity when targeted downstream from the AUG translation initiation site. This coding sequence may be particularly favorable for antisense ON binding, forming duplexes stable enough to sterically block translation. In addition, as noted above, morpholino oligomers have proven to be particularly effective RNA-binding molecules. While the invention is not limited to a particular mechanism, it is postulated that the RNA helix is distorted by the binding of the morpholino oligonucleotide, and that this distortion interferes with ribosomal binding.

Studies in support of the invention have suggested that the propyne groups of the C-5-P propyne modified ODN protrude into the major groove of the RNA duplex, and thus may also sterically interfere with ribosomal binding. Accordingly, substitution of other sterically bulky groups for the propyne group, including groups having different electronic structures, such as t-butyl, could produce a similar inhibitory effect.

V. Therapeutic Methods

The present invention provides a method for inhibiting p53 expression, particularly in cells characterized by p53 induction, and where inhibition of p53 produces a therapeutic benefit. The method can be used for treating a disease state characterized by p53 induction. The method comprises administering to the subject having such a condition, or to cells harvested from such a subject, an oligonucleotide with a sequence corresponding to SEQ ID NO: 1 or SEQ ID NO: 2. Preferably, the subject is a human subject. (As noted above, SEQ ID NO: 2 is not effective in rat models.) The oligonucleotide is preferably a morpholino oligonucleotide, a peptide nucleic acid, a 2'-O-allyl or 2'-O-alkyl modified oligonucleotide, a N3'→P5' phosphoramidate oligonucleotide, or a C-5-propyne pyrimidine-modified phosphorothioate oligonucleotide. Morpholino oligonucleotides are particularly preferred for both sequences. Also contemplated are C-5-P modified morpholino oligonucleotides.

As demonstrated by the data shown herein and reported in Arora, 1998, the anti-p53 ON suppress the expression of p53 in post-hepatectomy rats. Morpholino and C-5-P ON's were found to be more effective than equivalent amounts of the unmodified phosphorothioate (S-ODN), as determined by weight gain of the regenerating liver. The morpholino oligomer is surprisingly effective in view of the fact that it is targeted at a coding region (exon 10), well downstream of the AUG start region, the latter of which is the conventional target for RNAse-inactive ("steric blocker") antisense oligonucleotides.

A. Anti-proliferative Therapy

As noted above, an induction in p53 expression is observed in cells exposed to various DNA-damaging agents. The damaged DNA is most commonly repaired by unscheduled DNA synthesis. Such repair normally occurs during the $G_1$ cell cycle phase, which precedes the S (synthesis) phase. If, however, the modified DNA bases remain unrepaired (e.g. by eliminating the $G_1$-S cell cycle checkpoint, thus sending the cell prematurely into the S phase), consequences can include mutagenesis, due to erroneous replication of damaged DNA nucleotide base templates, and/or cell death, due to inability of the cell to replicate its genome past a damaged DNA site.

Inhibiting the expression of p53 suppresses this cell cycle checkpoint and can thus be used to selectively kill DNA-damaged cells. It was shown in U.S. Pat. No. 5,641,764 (Iversen) that administration of an antisense phosphorothioate oligonucleotide having the sequence OL(1)p53 (SEQ ID NO: 2) produced apoptosis ex vivo and in vivo in human liver cells. The effect was increased by exposure of the cells to conditions which increased the net reactive oxygen content in the cells. Such treatment produces little or no adverse effect on normal tissue, as normal tissue has greater oxygen scavenging activity than cancer cells. Most cells, for example, normally contain one or more enzymes, such as SOD, catalase, or glutathione peroxidase, which very rapidly combine with and inactivate excess reactive oxygen species. As described above, it is believed that the suppression of the $G_1$-S checkpoint by inhibition of p53 prevents repair of damaged DNA, leading to mutagenesis and cell death.

In a preferred method, therefore, particularly useful against cancer cells, the ON is administered in combination with an agent capable of increasing radical oxygen induced cytotoxicity. The oligonucleotide and agent can be administered substantially concomitantly, or sequentially, with either therapeutic agent being given first. However, best results are achieved when the oligonucleotide is administered sufficiently in advance to permit therapeutic blood levels to be achieved.

Increased radical oxygen levels are produced, for example, by exposure of the cell to radiation, or an agent capable of radical oxygen induced cytotoxicity, such as for example, anthracycline cytotoxic antibiotics (e.g., doxorubicin), BCNU, BSO (buthionine sulfoxamine), hydrogen peroxide, or antisense oligonucleotide inhibitors of SOD (superoxide dismutase), catalase, GSH synthetase, GSH reductase, or GSH peroxidase.

The agent capable of radical oxygen induced cytotoxicity can be, for example, a radiosensitizer, a chemotherapeutic agent which generates radical oxygen, or an oligonucleotide capable of interaction with cells of the host causing the formation of hydroxy radicals (e.g., see Iversen, U.S. Ser. No. 07/735,067, filed Jul. 25, 1991, entitled "Inhibition of Mutagenicity Induced by Binding of Oligonucleotides to Cells", the content of which is incorporated herein by reference). A number of cytotoxic agents that have a lethal effect on target cells within the patient, wherein the lethal effect may be enhanced by one or more sensitizing agents, may be used in the method of the invention. Included are radiation (whether the radiation therapy is delivered internally or administered by external means) and cytotoxic drugs. Examples of some of the many such drugs are nitrogen mustards such as L-phenylalanine nitrogen mustard (melphalan), anthracycline chemotherapeutics such as daunorubicin and doxorubicin, and platinum compounds such as cis-diaminodichloro platinum (cis-platin).

Internally delivered radiation includes therapeutically effective radioisotopes injected into a patient. Such radioisotopes include, but are not limited to, the radionuclide metals $^{186}$Re, $^{188}$Re, $^{64}$Cu, $^{67}$Cu, $^{109}$Pd, $^{212}$Bi, $^{203}$Pb, $^{212}$Pb, $^{211}$At, $^{97}$Ru, $^{105}$RH, $^{198}$Au, $^{199}$Ag, and $^{131}$I. These radioisotopes generally will be bound to carrier molecules (e.g., in the form of a chelate-antibody conjugate) when administered to a patient. Examples of suitable internally delivered radiotherapeutic agents are metal radionuclide chelates conjugated to antibodies as described, for example, in EP Publication No. 188,256. Radiation administered by external means includes external beam radiation such as cobalt therapy.

The choice of sensitizing agent depends on such factors as the particular type of tumor to be treated and the cytotoxic agent to be administered. Preferably, the compound is selective for a certain target site in vivo, such as a cancer cell. For example, U.S. Pat. No. 4,628,047 reports the use of diltiazem to enhance the sensitivity of a variety of types of cancer cells toward cytotoxic agents such as doxorubicin. Other pairings of sensitizers with cytotoxic drugs, as well as expected differences in the susceptibility of different types of cancer cells to treatment with these agents, are discussed in *Important Advances in Oncology* (DeVita et al., editors, J. B. Lippincott Co., Philadelphia (1986), pp. 145–157).

A preferred sensitizer is BSO (buthionine sulfoxamine, available from Chemical Dynamics Corporation, South Plainfield, N.J.), a synthetic amino acid that inhibits γ-glutamylcysteine synthetase and leads to a marked decrease of glutathione (GSH) in cells. Thus, BSO is thought to function as a sensitizer for drugs that have a cytotoxic effect enhanced by decreasing cellular glutathione levels. Especially preferred is the S-isomer of BSO, which has utility in depleting glutathione in the cell (see U.S. Pat. Nos. 5,171,885 and 5,245,077).

Additional combinations of sensitizers and cytotoxic agents may be identified through such methods as in vitro assays using cultured cells which correspond to the desired target cells (e.g., a specific cancer cell line). For example, Russo et al. describe assays for determining whether BSO is effective in lowering glutathione synthetase levels in a particular type of cell line.

The above discussion of radical oxygen generating species, cytotoxic agents and sensitizers is primarily directed to the preferred target cells, i.e., cancer cells characterized by p53 expression. Such cancers include those of the bladder, brain, breast, cervix, colon, esophagus, larynx, liver, lung, ovary, pancreas, prostate, skin, stomach and thyroid.

In another preferred method, administration of the antisense ON is accompanied by administration of an agent effective to interfere with progression from the $G_2$ phase to the M (mitosis) phase of the cell cycle. Such agents include, for example, pentoxifylline (Russell, 1996), silymarin (Ahmad, 1998), staurosporine (Swe, 1997), phenylahistin (Kanoh, 1997), paclitaxel (Shu, 1997), retinoic acid (Zhu, 1997), flavopiridol (Sedlacek, 1996), methyl-2,5-dihydrocinnamate (Koch, 1996), herboxidiene (Horiguchi, 1996), 9-nitrocamptothecin (Khooustov, 1995), maitotoxin (VanDolah, 1996), apigenin (Sato, 1994), nocodazole, and colcemid (Zhang, 1998). Recent reports (Cross, 1995) have suggested that p53 is instrumental in a spindle checkpoint, which ensures complete assembly of the spindle apparatus during the mitosis (M) phase of the cell cycle. In studies in support of the invention, p21-deficient mice, when treated with $G_2$-M inhibitors such as those listed above, showed a high degree of aneuploidy in the affected cells. It is postulated that the inhibitors prevented the cells from undergoing normal progression through the mitosis phase, and, lacking the mitotic (and $G_1$-S phase) checkpoint, the cells underwent successive synthesis (S) phases, resulting in aneuploidy. Because p53 is necessary for transcriptional activation of p21, cells in which p53 has been inhibited by the antisense agents of the invention should show a similar effect.

Spindle inhibitors such as nocodazole or colcemid (Cross, Zhang) may also be used in conjunction with anti-p53 antisense agents. In the absence of the p53-dependent spindle checkpoint, such cells are expected to undergo successive cell cycles with abnormal or incomplete mitotic phases, also leading to polyploidy or aneuploidy.

Other hyperproliferative disorders may also be treated. Examples of hyperproliferative skin disorders include human papilloma virus (HPV)-infected cells, commonly associated with warts, superficial neoplasias of the skin such as melanomas, pre-malignant and malignant carcinomas, actinic keratosis, lupus erythematosus, dermatitis, and psoriasis. Hyperproliferative diseases of other epithelial tissues (e.g. endothelium, mesothelium) include reversible obstructive airway disease, such as asthma and bronchitis. Various hyperproliferative disorders of the eye, including conical cornea, keratoconjunctivitis, vernal conjunctivitis, and keratitis leukoma, may also be treated. The methods may also be used to treat hyperproliferative vascular diseases such as intimal smooth muscle cell hyperplasia, vascular occlusion, and restenosis.

B. Treatment of Hypoxic or Ischemic States

Other disease states characterized by p53 induction include hypoxic states such as follow an ischemic attack such as a stroke. For example, p53 was observed to be preferentially expressed in apoptotic cells after ischemia in the cerebrum (Li), and in damaged neurons in models of ischemia and epilepsy (Xiang). Raafat observed increased levels of p53 following ischemia/reperfusion in kidneys, and proposed that the increase may facilitate apoptosis. Heat shock has also been reported to induce p53 (Graeber). Therefore, in another aspect, the invention includes treatment of tissues subjected to such stresses, e.g., heat shock, epileptic seizure, stroke, and other occurrences of ischemia and/or reperfusion (e.g. following organ transplant) with anti-p53 antisense agents as described herein.

VI. Formulations and Administration

A. Therapeutic Formulations

For administration in accordance with the treatment methods of the invention, the antisense oligonucleotides are preferably combined with a pharmaceutically acceptable carrier, such as a suitable liquid vehicle or excipient, and optional auxiliary additives. The liquid vehicles and excipients are conventional and commercially available. Illustrative thereof are distilled water, physiological saline, aqueous solutions of dextrose, and the like.

In general, in addition to the active compounds, the pharmaceutical compositions of the invention may contain suitable excipients and auxiliaries which facilitate processing of the active compounds into preparations which can be used pharmaceutically. Suitable excipients are, in particular, fillers such as sugars, for example, lactose or sucrose, mannitol or sorbitol, cellulose preparations and/or calcium phosphates, and binders such as starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, alginic acid, or a salt thereof. Auxiliaries include flow-regulating agents and lubricants, for example, silica, talc, stearic acid or salts thereof, and/or polyethylene glycol.

Dragee cores may be provided with suitable coatings which, if desired, may be resistant to gastric juices. For this purpose, concentrated sugar solutions may be used, which may optionally contain gum arabic, talc, polyvinylpyrrolidone, polyethyleneglycol, and/or titanium dioxide, lacquer solutions, and suitable organic solvents or solvent mixtures. In order to produce coatings resistant to gastric juices, solutions of suitable cellulose preparations, such as acetylcellulose phthalate or hydroxypropylmethylcellulose phthalate, are used. Dyestuffs and pigments may be added to the tablets of dragee coatings for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Pharmaceutical preparations which can be used rectally include, for example, suppositories, which consist of a combination of the active compounds with a suppository base. Suitable suppository bases include natural or synthetic triglycerides, paraffin hydrocarbons, polyethylene glycols, or higher alkanols. In addition, it is possible to use gelatin rectal capsules which consist of a combination of the active compounds with a base. Possible base materials include liquid triglycerides, polyethylene glycols, or paraffin hydrocarbons.

Suitable liquid formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, such as sodium carboxymethyl cellulose, sorbitol, and/or dextran. The suspension may also contain stabilizers.

In addition to administration with conventional carriers, the active ingredients may be administered by a variety of specialized delivery techniques. For example, the compounds of the present invention may be administered encapsulated in liposomes. The active ingredient, depending upon its solubility, may be present both in the aqueous phase and in the lipidic layer(s), or in what is generally termed a liposomic suspension. The lipidic layer generally comprises phospholipids, such as lecithin or sphingomyelin, steroids such as cholesterol, ionic surfactants such as diacetylphosphate, stearylamine, or phosphatidic acid, and/or other hydrophobic materials. The diameters of the liposomes generally range from about 15 nm to about 5 microns.

Methods for preparing such dosage forms are known or will be apparent to those skilled in the art; for example, see Remington's Pharmaceutical Sciences (19th Ed., Williams & Wilkins, 1995). The pharmaceutical preparations are manufactured according to procedures well known in the art. For example, they may be made by means of conventional mixing, granulating, dragee-making, dissolving, or lyophilizing processes. The process to be used will depend ultimately on the physical properties of the active ingredient used.

B. Treatment of Tumors

The composition may be administered to a subject orally, transdermally or parenterally, e.g., by intravenous, subcutaneous, intraperitoneal, or intramuscular injection. For in vivo antineoplastic use, the p53 mRNA antisense oligonucleotides are preferably administered intravenously.

In accordance with the present invention, the oligonucleotide which inhibits expression of p53, thus acting as an oxidative repair path down-regulator, is administered to a patient prior to or concomitant with administration of the agent capable of radical oxygen induced cytotoxicity. When administered simultaneously, the two active agents can be in conjugated or unconjugated form. If in conjugated form, it is preferred that the conjugate comprises a cleavable linkage so that the oligonucleotide and the cytotoxic agent are released at the target site.

The amount of each agent administered is such that the combination of the two types of agents is therapeutically effective. Dosages will vary in accordance with such factors as the age, health, sex, size and weight of the patient, the route of administration, the toxicity of the drugs, and the relative susceptibilities of the cancer to the oligonucleotide and cytotoxic agent. Recomrnended dosages and dosage forms for most of the cytotoxic agents have been established and can be obtained form conventional sources, such as the *Physicians Desk Reference*, published by Medical Economics Company, Inc., Oradell, N.J. If necessary, these parameters can be determined for each system by well-established procedures and analysis, e.g. in clinical trials.

For in vivo use, the preferred dosage of the oligonucleotides of the invention is typically that which is necessary to attain a concentration in the blood of from about 0.01 to about 1 $\mu$mol/l. This concentration can be achieved in a variety of ways; doses of between about 0.05 and about 0.2 mg/kg/hour by continuous IV infusion have been found to be acceptable. Greater or lesser amounts of oligonucleotide may be administered as required.

Example 3, below, demonstrates the application of the invention in the treatment of human B-cell lymphoma.

C. Treatment of Ischemic Injury

The ischemic condition may be due to an interruption in cerebral circulation, such as caused by cardiac failure, or other condition leading to global loss of blood supply to the brain, or to localized interruptions in blood flood, such as due to cerebral hemorrhaging, or localized thrombotic or embolic events, or head trauma. The ischemic condition to be treated is generally associated with stroke, defined as the sudden diminution or loss of neurological function caused by an obstruction or rupture of blood vessels in the brain. Secondary brain damage resulting from the original ischemic event typically includes cerebral cell destruction, or lesions, in the area surrounding the ischemic injury, in the case of focal ischemia, and also in areas of selective vulnerability in lesions, such as the hippocampus or basal ganglia, in the case of global ischemia. The secondary damage may often be manifested by functional impairment, such as loss of short-term or long-term memory.

The ON is formulated for parenteral administration in a suitable inert carrier, such as a sterile physiological saline solution. The dose administered will be determined by route of administration. One suitable route is intracerebroventricular (ICV), at a dose level of about 50 $\mu$g–5 mg ON/kg body weight. A pharmaceutically effective dose, i.e., a dose effective to produce significant reduction in anatomical and/or functional damage, can be estimated from the dose/response seen in model systems for ischemia and stroke damage. Such model systems include the gerbil model of global ischemia, produced by transient occlusion of carotid arteries of the neck, and the rat four-vessel occlusion model. Tissues are examined for anatomical damage, and functional damage may be assessed by observation of hyperactivity, a common consequence of cerebral ischemia in animals, or effect on short-term memory. These procedures are known in the art; see for example, U.S. Pat. No. 5,051,403.

D. Treatment of Restenosis

An important aspect of successful anti-restenosis therapy, particularly with regard to antisense agents, is effective delivery of the antisense oligomer to the affected cells. Systemically administered anti-restenosis drugs typically fail to achieve an effective concentration at the site of vessel injury without using unacceptably high concentrations of the drug. Delivery devices, such as those described in co-owned and copending U.S. application Ser. No. 09/062,160, entitled "Method of Treating Restenosis by Antisense Targeting of CMV", can be used to deliver the oligomer to the site of angioplasty in a patient. The oligomer is preferably a morpholino oligomer, and is preferably contained in a pharmaceutically acceptable carrier. The oligomer may also be contained in a biocompatible polymeric carrier, also described in the above-referenced application.

Preferably, the oligomer is delivered concurrent with the angioplasty procedure. As reported by Farrell, uptake of an oligonucleotide by cells can be significantly increased when the compound is administered to balloon-injured arteries, relative to uptake by normal arteries. Drug therapy using the compositions of the invention may be combined with radiation or photodynamic therapy.

Dosages are determined according to the size of the subject, the route of administration, and the extent of the affected tissue, according to standard pharmaceutical practices. The preferred level of drug is that effective to inhibit p53 expression, and reduce or prevent restenosis, without unacceptable side effects. For an adult human, a recommended dosage is in the range of 1–25 $\mu$mol of antisense oligomer, and preferably 2–15 $\mu$mol. Optimum dosages for a given route can be determined by routine experimentation according to methods known in the art. For example, for delivery to the site of vessel injury, in vivo models such as described in Edelman and Rosenberg may be used.

When the oligomer is incorporated into a drug delivery device, the device is effective to deliver an appropriate dosage of drug, as described above. With respect to the surface area of tissue to be treated, an effective dose is typically in the range of 30 to 3000 $\mu$g oligomer per cm$^2$ of vessel wall, and more preferably about 300 to 1500 $\mu$g/cm$^2$. The patient may also be given the composition on a periodic basis after angioplasty, at a dosage level sufficient to further inhibit restenosis.

While the invention has been described with reference to specific methods and embodiments, it will be appreciated that various modifications may be made without departing from the invention.

EXAMPLES

Example 1

Oligonucleotide Synthesis

All chain-extension syntheses were performed on an Applied Biosystems Model 380B DNA synthesizer (Foster City, Calif.) using 1-$\mu$mole column support and the cyanoethyl approach employing phosphoramidite chemistry as described by ABI User Bulletin, No. 58, 1991. The synthesizer was programmed with the protocol in the user's manual.

A summary of a typical synthesis is as follows: A 1 $\mu$mol silica gel support column with the 3' base of the ODN (i.e. unmodified nucleotide, C-5-propyne nucleotide, or morpholino nucleotide analog) linked by the 3' hydroxy group is inserted, and synthesis is carried out in a base by base fashion from the 3' to 5' direction. All liquid reagents are supplied by Applied Biosystems, Inc. The argon gas is supplied by Air Products (Omaha). The first step is the flushing of the column with acetonitrile then argon gas which removes any residue in the column. Next, trichloroacetic acid protonates the dimethoxytrityl (DMT) group, which caps the 5' oxygen of the nucleotides during the ODN synthesis. The protonated DMT is then removed from the base. The column is flushed again with acetonitrile and argon. The DMT waste is collected by the DMT waste port into test tubes and checked if it is a bright orange color. This color check is performed to insure if detritylation was successful. The DMT groups can be quantified spectrophotometrically by reading absorbency at 498 nm. If the color is not bright orange, then detritylation of the bases may have not been successfully performed and synthesis of impure ODNs may occur. The next step of the synthesis is the coupling of the next base in the ODN sequence. An appropriate nucleotide base, modified to a cyanoethyl phosphoramidite, is dissolved in acetonitrile and delivered with tetrazole to the column. The bases react to form an internucleotide phosphite bond. The column is flushed with acetonitrile and argon. Any uncoupled 5' hydroxy groups are capped with an acetyl group by flushing the column with acetic anhydride and 1-methylimidizole. This cap will prevent these uncoupled bases from any continuation in synthesis and reduce the length of impurities. The columns are flushed again and the trivalent phosphite is oxidized to the pentavalent phosphorothioate triester with tetraethylthiuram disulfide and acetonitrile. The column is flushed with acetonitrile and argon. The synthesis is then repeated again for the next base in the sequence starting with the detritylation step. The S-ODNs are cleaved from the column by passing ammonium hydroxide through the column and collecting the eluate. The ammonium hydroxide and cyanoethyl (from the phosphate links) are removed by evaporation of the S-ODN solution in a vacuum centrifuge for overnight. The dried ODN is diluted in sterile saline. Purity of the S-ODN is checked by running a sample of the S-ODN diluted in water on a 10% polyacrylamide gel. The concentration of S-ODN is determined by reading the absorbance at 260 nm and multiplying the absorbance by its extinction coefficient.

Further details on preparation of morpholino oligonucleotide analogs can be found, for example, in Summerton and Weller, *Antisense & Nucleic Acid Drug Dev.* 7:187–195 (1997).

Example 2
Partial Hepatectomy

The partial hepatectomy study was performed on male Sprague Dawley rats (Sasco, Omaha Nebr.) weighing between 200–220 grams. The animals were housed in clear plastic cages in UNMC's AAALAC-approved facility with 12 hour light/dark cycle and allowed access to Purina rat chow and tap water ad libitum. All animal protocols were approved by the 'Institutional Animal Care and Use Committee' of the university.

The procedure was performed as described by Higgins and Anderson (1931). Aseptic surgical techniques were employed. Rats were anesthetized using methoxyflurane (Mallinckrodt Veterinary, Mundelein, Ill.) and positioned with their ventral surface exposed. A three to four cm. long area was shaved along the median-line immediately posterior to the xiphoid process and swabbed with betadine. An incision was made along the median line to expose the liver. The medial and left lateral lobes were securely ligated and then excised. This resulted in removal of approximately 65 to 70 percent of the total liver. The abdominal incision was closed in two layers. Control rats that did not to receive a partial hepatectomy underwent an identical but sham surgery; their livers were only exposed and not partly excised.

Oligonucleotide administration: The ODNs were injected intraperitoneally at doses of 1 mg/200 gm/day S-ODN, 0.1 mg/220 g/day C-5-P S-ODN, and 50 nM (approx. 3.4 mg)/200 g/day morpholino. All rats were administered respective ODNs immediately upon regaining consciousness after the surgery, and every 24 hr thereafter, depending on the length of the experiment. Rats were then allowed to recuperate for 1, 2, 5 or 7 days from the time of surgery. Wet weight gain was determined 24 h following administration of ODN to produce the data shown in FIG. 2.

Example 3
Treatment of human B-cell lymphoma.

Drug Treatment Regimen: Starting on Day 0, patients receive a morpholino antisense oligonucleotide having SEQ ID NO:1 at a dose of 0.2 mg/kg/hr as a 7 day continuous IV infusion through a venous access device. MINE chemotherapy is given beginning on Day 4, in accordance with the following schedule:

Mesna Injection (MESNEX™, Bristol-Meyers Oncology): 500 mg/M² IV 30 minutes prior to ifosfamide, 250 mg/M² IV four hours after ifosfamide, and 250 mg/M² orally eight hours after the ifosfamide on each of days 4–7.

Ifosfamide (IFEX™, Bristol-Meyers Oncology): 1.33 g/M² IV on each of days 4–7.

Mitoxantrone hydrochloride (NOVANTRONE™, Lederle Laboratories) 10 mg/M² IV on day 4 only.

Etoposide (VEPESID™, Bristol-meyers Oncology) 80 mg/M² IV on each of days 4–7.

Patients are regularly evaluated for toxicity and response of their disease. Patients receive weekly CBC (complete blood count) and platelet counts. Cycles are repeated every 4 weeks for a maximum of 6 cycles. Patients are assessed with respect to response every cycle for disease measurable by physical examination. Patients are classified with respect to response (complete response, partial response, stable response, or progressive disease).

Patients are expected to show enhanced clinical response with this therapy as opposed to traditional MINE therapy, which does not include use of the antisense oligonucleotide SEQ ID NO:1 (OL(1)p53). OL(1)p53 is expected to sensitize the cancer cells to the effects of MINE by inhibiting the cell cycle repair mechanism, thereby preferentially killing cancer cells via p53-independent apoptosis.

What is claimed is:

1. A method of inhibiting expression of p53 in a mammalian subject, comprising administering to the subject, in a suitable pharmaceutical carrier, a pharmaceutically effective amount of an antisense agent having the base sequence SEQ ID NO:1, identified as 5'-TCA GTC TGA GTC AGG CCC-3, or the base sequence SEQ ID NO:2, identified as 5'-CCC TGC TCC CCC CTG GCT CC-3', wherein the antisense agent is a morpholino oligonucleotide.

2. The method of claim 1, wherein the morpholino oligonucleotide comprises morpholino subunits joined by phosphorodiamidate backbone linkages.

3. The method of claim 1, wherein the antisense agent has the sequence SEQ ID NO: 1.

4. The method of claim 1, wherein the antisense agent has the sequence SEQ ID NO: 2.

5. The method of claim 1, wherein said subject is a human subject.

6. The method of claim 1, further comprising treating said subject with an agent effective to increase radical oxygen species at the cellular level.

7. The method of claim 6, wherein said agent is selected from a radiosensitizing agent, ionizing radiation, a hyperbaric oxygen environment, and a chemotherapeutic agent which increases radical oxygen species at the cellular level.

8. The method of claim 7, wherein said chemotherapeutic agent is an anthracycline or anthraquinone.

9. The method of claim 1, further comprising treating said subject with an agent effective to interfere with progression from the G2 phase to the M phase of the cell cycle.

10. The method of claim 9, wherein said agent is selected from the group consisting of a phosphokinase C (PKC) inhibitor, bis(chloroethyl)nitrosourea (BCNU), pentoxifylline, silymarin, staurosporine, phenylahistin, paclitaxel, retinoic acid, flavopiridol, methyl-2,5-dihydrocinnamate, herboxidiene, 9-nitrocamptothecin, maitotoxin, apigenin, nocodazole, and colcemid.

11. A composition for use in inhibiting expression of p53 in a subject, comprising an antisense agent having a base sequence selected from the group consisting of SEQ ID NO:1, identified as 5'-TCA GTC TGA GTC AGG CCC-3', and SEQ ID NO:2, identified as 5'-CCC TGC TCC CCC CTG GCT CC-3', wherein the antisense agent is a morpholino oligonucleotide, and a suitable pharmaceutical carrier.

12. The composition of claim 11, wherein the morpholino oligonucleotide comprises morpholino subunits joined by phosphorodiamidate backbone linkages.

13. The composition of claim 11, wherein the antisense agent has the sequence SEQ ID NO: 1.

14. The composition of claim 11, wherein the antisense agent has the sequence SEQ ID NO: 2.

15. A morpholino oligonucleotide having a base sequence selected from the group consisting of SEQ ID NO:1, identified as 5'-TCA GTC TGA GTC AGG CCC-3', and SEQ ID NO:2, identified as 5'-CCC TGC TCC CCC CTG GCT CC-3'.

16. An oligonucleotide as recited in claim 15, having the base sequence SEQ ID NO: 1.

17. An oligonucleotide as recited in claim 15, having the base sequence SEQ ID NO: 2.

18. A morpholino oligonucleotide as recited in claim 15, which comprises morpholino subunits joined by phosphorodiamidate backbone linkages.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 1
tcagtctgag tcaggccc                                              18

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 2
ccctgctccc ccctggctcc                                            20
```